(12) United States Patent
Fisher

(10) Patent No.: US 11,769,574 B2
(45) Date of Patent: *Sep. 26, 2023

(54) TRANSMITTING MEDICAL DIGITAL ARTIFACTS TO A MOBILE DEVICE

(71) Applicant: Michelle Fisher, Berkeley, CA (US)

(72) Inventor: Michelle Fisher, Berkeley, CA (US)

(73) Assignee: Michelle Fisher, Berkeley, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 17/142,975

(22) Filed: Jan. 6, 2021

(65) Prior Publication Data
US 2021/0174918 A1   Jun. 10, 2021

Related U.S. Application Data

(63) Continuation of application No. 14/078,440, filed on Nov. 12, 2013, now Pat. No. 10,892,044, which is a continuation of application No. 13/218,879, filed on Aug. 26, 2011, which is a continuation-in-part of application No. 13/216,098, filed on Aug. 23, 2011, now abandoned, which is a continuation-in-part of
(Continued)

(51) Int. Cl.
*G16H 10/60* (2018.01)
*G16H 10/65* (2018.01)
*G16Z 99/00* (2019.01)

(52) U.S. Cl.
CPC .............. *G16H 10/60* (2018.01); *G16H 10/65* (2018.01); *G16Z 99/00* (2019.02)

(58) Field of Classification Search
CPC .............................. G16H 10/60; G16H 10/65
See application file for complete search history.

(56) References Cited

U.S. PATENT DOCUMENTS 8,566,239 B2   10/2013   Arthur
9,294,917 B2   3/2016   Nystrom
(Continued)

FOREIGN PATENT DOCUMENTS

WO   WO 2006/108858   4/2006
WO   WO-2006108858 A1 * 10/2006   ......... G06F 19/3418

OTHER PUBLICATIONS

U.S. Appl. No. 14/078,440 Notice of Allowance dated Nov. 24, 2008, 8 p.
(Continued)

*Primary Examiner* — Evangeline Barr

(57) ABSTRACT

This invention describes how users can capture digital artifacts from any medical device using their mobile device. Some examples of medical devices included, but are not limited to a medical ID card, Medical ID bracelet, Electronic Medical Records, blood pressure machines, blood glucose, scales, inhalers, INR, prescription bottles and trays, pulse oximeter , etc. Digital artifacts included, but are not limited to a medical ID, basic patient information, patient contact information, emergency contact information, primary care physician information, health insurance information including co-pay and deductibles, prescriptions, office visit summary, appointment cards, Electronic Medical Records (EMR), lab results, blood type, organ/donor status, vital signs, diagnostic data, immunization records, payments and transaction history, pictures, etc

24 Claims, 9 Drawing Sheets

Related U.S. Application Data application No. 13/215,069, filed on Aug. 22, 2011, now abandoned, which is a continuation-in-part of application No. 13/213,840, filed on Aug. 19, 2011, now abandoned, which is a continuation-in-part of application No. 13/208,247, filed on Aug. 11, 2011, now abandoned, which is a continuation-in-part of application No. 13/184,209, filed on Jul. 15, 2011, now abandoned.

(60) Provisional application No. 61/442,384, filed on Feb. 14, 2011.

(56) References Cited

U.S. PATENT DOCUMENTS

| | | |
|---|---|---|
| 2003/0130708 A1 | 7/2003 | Von Ark |
| 2006/0000900 A1 | 1/2006 | Fernandes |
| 2007/0135866 A1* | 6/2007 | Baker .................. A61B 5/1113 600/407 |
| 2008/0116264 A1 | 5/2008 | Hammad et al. |
| 2009/0054737 A1 | 2/2009 | Magar |
| 2009/0075592 A1 | 3/2009 | Nystrom et al. |
| 2009/0164253 A1 | 6/2009 | Lyshkow |
| 2009/0177495 A1 | 7/2009 | Abousy |
| 2010/0152551 A1 | 6/2010 | Hsu |
| 2011/0167133 A1 | 7/2011 | Jain |
| 2012/0185267 A1 | 7/2012 | Kamen |
| 2015/0012440 A1 | 1/2015 | Kelley |
| 2016/0080364 A1* | 3/2016 | Karimzadeh ......... G06F 21/606 726/6 |

OTHER PUBLICATIONS

U.S. Appl. No. 14/078,440 Board Decision dated Nov. 10, 2020, 7 p.
Wikipedia Infrared https://en.wikipedia.org/wiki/Infrared_Data_Association.
Wikipedia Bluetooth http://nearfieldcommunication.org.bluetooth.html.
Wikipedia NFC https://en.wikipedia.org/wiki/Near-field communication.
RF wireless comparison of NFC vs RFID http://www.rfwireless-world.com/terminology/NFC-vs-RFID-vs-Bluetooth-vs-wifi.html.
SMS-https://en.m.wikipedia.org/wiki/Text messaging.
MMS-https://en.wikipedia.org/wiki.Multimedia Messaging Service#Technical description.
Email—https://techterms.com/definition/email.
Smart Card https://en.wikipedia.org/wiki/Smart card.

* cited by examiner

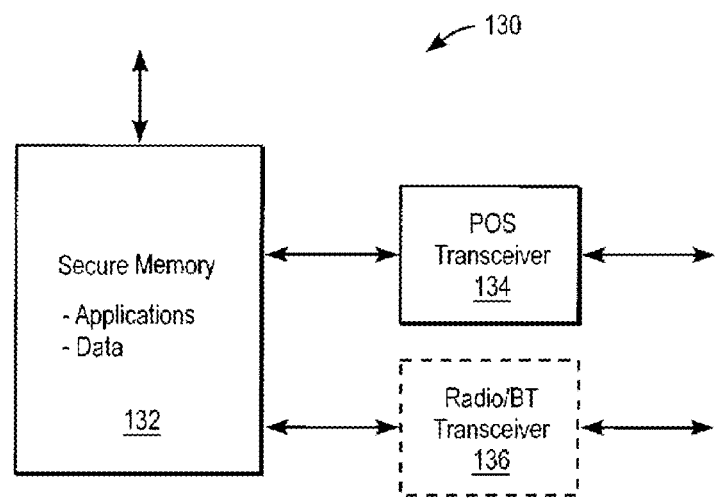
FIG. 2B1
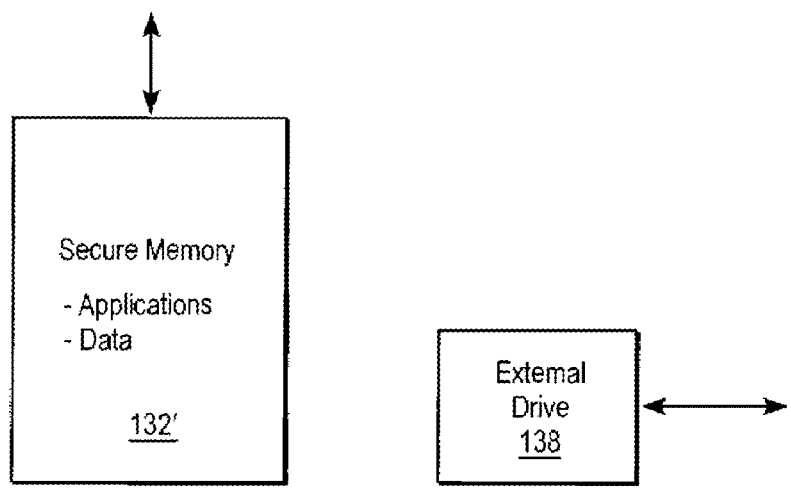
FIG. 2B2A

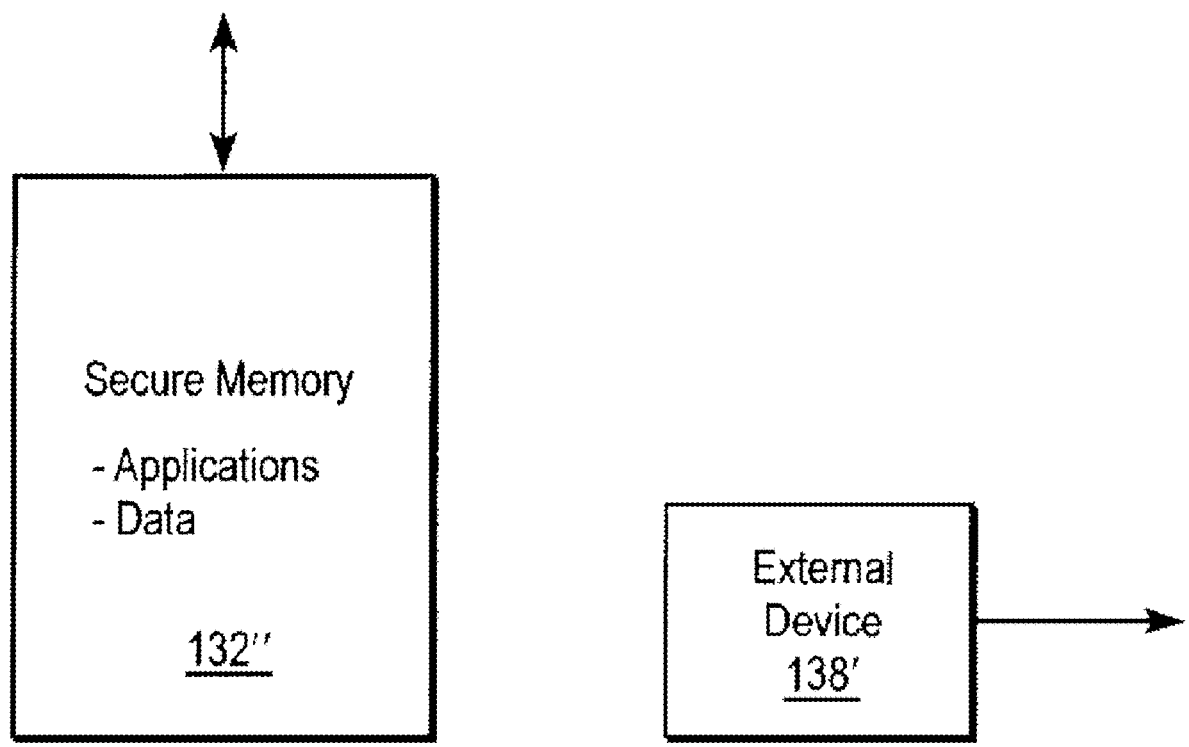
FIG. 2B2B

| Health Care Secure Element Application ID | Function |
|---|---|
| SE_App1 | Transfer medical ID to another NFC enabled device requiring authentication prior to transmission |
| SE_App2 | Transfer medical ID to another NFC enabled device without authentication prior to transmission |
| SE_App3 | Transfer prescriptions to another NFC enabled device requiring authentication prior to transmission |
| SE_App4 | Purchase prescriptions using an NFC enabled device requiring authentication prior to transmission |
| SE_App5 | Transfer EMR to another NFC enabled device requiring authentication prior to transmission |
| SE_App6 | Transfer diagnostic data to another NFC enabled device requiring authentication prior to transmission |
| SE_App7 | Transfer diagnostic data to another NFC enabled device without authentication prior to transmission |
| SE_App8 | Transfer immunization and other shots to NFC enabled device with authentication prior to transmission |
| SE_App9 | Transfer Xrays to NFC enabled device with authentication prior to transmission |
| SE_App10 | Pay with contactless payment method such as Pay Pass |
| SE_App11 | Get nutritional values from products |
| SE_App12 | Get medical dosages from medicine container |
| SE_App13 | Get appointment card |
| SE_App14 | Basic Patient Info (e.g. blood type, birth date,etc) |
| SE_App15 | Medical Conditions |
| SE_App16 | Allergies |
| SE_App17 | Emergency Contact Info |
| SE_App18 | Medications |
| SE_App19 | Health Plan Information |
| SE_App20 | Dynamic Verification Code |
| SE_App21 | Get blood pressure data |
| SE_App22 | Register medical sensor |

TRANSMITTING MEDICAL DIGITAL ARTIFACTS TO A MOBILE DEVICE

CLAIM OF PRIORITY

This application is a continuation in part and claims priority to U.S. patent application Ser. No. 14/078,440 entitled, "Connected Medical Devices " filed on Nov. 12, 2013 which is a continuation in part and claims priority to U.S. patent application Ser. No. 13/218,879 entitled "Using an NFC Enabled Mobile Device To Manage Digital Medical Artifacts" filed on Aug. 26, 2011 which is a continuation in part and claims priority to U.S. patent application Ser. No. 13/216,098 entitled "Streamlining NFC Transactions Using A Mobile Communication Device" filed on Aug. 23, 2011 which is a continuation in part and claims priority to U.S. patent application Ser. No. 13/215,069 entitled "Transferring Data From an NFC Enabled Mobile Device to a Remote Device" filed on Aug. 22, 2011 which is a continuation in part of U.S. patent Ser. No. 13/213,840, entitled "Transferring Data Between NFC Enabled Mobile Devices With Multiple Secure Elements" filed on Aug. 19, 2011 which is a continuation in part and claims priority to U.S. patent Ser. No. 13/208,247, entitled "Transferring Data Between NFC Enabled Mobile Devices " filed on Aug. 11,2011 which is a continuation in part of U.S. patent Ser. No. 13/184,209 , entitled "Method and Systems of loading and unloading digital artifacts between a mobile device with an associated secure element and other remote devices" filed on Jul. 15, 2011 which claims priority to U.S. Provisional Patent Application No. 61/442,384, entitled "Method and Systems of loading and unloading digital between a mobile device with an associated secure element and other remote devices" filed on Feb. 14, 2011. All of the above-referenced patent applications are incorporated by reference herein in their entirety

RELATED APPLICATIONS

Other patents referenced include U.S. patent application Ser. No. 13/223,233, " Using an NFC Enabled Mobile Device To Manage Health Care" filed on Aug. 31, 2011, U.S. patent application Ser. No. 11/944,267, entitled "Method and System for Delivering Information to a mobile communication device based on consumer transactions", filed Nov. 21, 2007 and U.S. patent application Ser. No. 11/956,261 entitled "Method and System for Delivering Customized Information To A Mobile Communication Device Based on User Affiliations", filed Dec. 13, 2007. All of the above-referenced patent applications are incorporated by reference herein in their entirety

FIELD OF INVENTION

The present invention relates to data communications and wireless devices.

BACKGROUND OF THE INVENTION

Mobile communication devices—e.g., cellular phones, personal digital assistants, and the like—are increasingly being used to conduct payment transaction. Such payment transactions can include, for example, purchasing goods and/or services, tickets, bill payments, and transferring funds between bank accounts. Because of bigger screens, better user input with touch screens increased processing capability, and faster more reliable wireless mobile devices, can be used to manage electronic medical records.

BRIEF SUMMARY OF THE INVENTION

Medical devices capture and/or store data. Some examples of medical devices included, but are not limited to a medical Identification (ID) card, Medical ID bracelet, Electronic Medical Records, blood pressure machines, blood glucose, scales, inhalers, INR, prescription bottles and trays, pulse oximeter , or any device that captures and stores medical data.. However, medical devices don't export data or not very easily. So, the Health Care Provider (HCP) is required to manually write down the sensor/measurement data displayed on the medical device and/or enter it into a computer which is time consuming, prone to error, and costly.

While some medical devices have the ability to export data to a personal computer using a cable or wirelessly using Blue tooth™ for example, these few devices have special customized interfaces which are costly and limit the patient and health care provider to using those devices which may not be their preferred medical device. In many instances patients and health care providers prefer to use certain medical devices based on their functionality, cost, or accuracy in capturing measurement data particularly for very serious chronic illnesses where accuracy is extremely important.

This invention describes various ways to capture data from any medical device and transmit it electronically to mobile devices (e.g. cell phones, smart phones, electronic note books), computers, servers , electronic medical records, etc. by using a secure element that serves as a "universal health port". Thus, making a solution that is more scalable, flexible, cost effective, and beneficial to patients, health care providers, etc.

This application is a continuation in part and claims priority to U.S. patent application Ser. No. 13/216,098 entitled "Streamlining NFC Transactions Using A Mobile Communication Device" filed on Aug. 23, 2011 which is a continuation in part and claims priority to U.S. patent application Ser. No. 13/215,069 entitled "Transferring Data From an NFC Enabled Mobile Device to a Remote Device" filed on Aug. 22, 2011 which is a continuation in part of U.S. patent Ser. No. 13/213,840, entitled "Transferring Data Between NFC Enabled Mobile Devices With Multiple Secure Elements" filed on Aug. 19, 2011 which is a continuation in part and claims priority to U.S. patent Ser. No. 13/208,247, entitled "Transferring Data Between NFC Enabled Mobile Devices " filed on Aug. 11, 2011 which is a continuation in part of U.S. patent Ser. No. 13/184,209, entitled "Method and Systems of loading and unloading digital artifacts between a mobile device with an associated secure element and other remote devices" filed on Jul. 15, 2011 which claims priority to U.S. Provisional Patent Application No. 61/442,384, entitled "Method and Systems of loading and unloading digital between a mobile device with an associated secure element and other remote devices" filed on Feb. 14, 2011. All of the above-referenced patent applications are incorporated by reference herein in their entirety

BRIEF SUMMARY OF THE INVENTION

The system is configured with a mobile device (with client application also referred to as a mobile wallet), a secure element that is associated with the mobile device, Near Field Communication (NFC) Point Of Sale System (POS) which is capable of processing financial transactions (including 2-way wireless terminal capable of sending and transmitting), NFC Point-Of-Presence (POP) Terminal which is capable of processing non-financial transactions (including 2-way wireless terminal capable of sending and transmitting), an NFC Point-of-Entry (POE) Device which is capable of providing access to venues including 2-way wireless terminal capable of sending and transmitting, a management server, a Trusted Service Manager (TSM) and several 3rdParty artifact provider/aggregator.

In the delivery scenario, when the user holds an NFC enabled mobile communication device with a secure element coupled to it in proximity of a suitable equipped POS/POE/POP with NFC, the NFC POS/POE/POP device will trigger an application residing in the secure element (which is different than an application residing on the mobile communication device) to power on and activate an application residing in the secure element, transfer data or digital artifacts (e.g debit/prepaid/credit card, receipts, tickets, advertisements, coupons, loyalty points, gift cards, vouchers, content (video, image, ringtone, movie), games, documentation, business cards, tickets, hotel key, health care records, security key, automobile key, etc.) from/to the secure element, and the secure element may issue commands and/or respond to commands just to name a few.

Using this system, at the time of a transaction, a user can use the mobile wallet software (on a mobile computing device) and associated secure element, in conjunctions with the POP/POS/POE to:

Store medical ID
Store patient contact information such as address, phone number, employer contact info
Store emergency contact information
Store basic patient information such as gender, age, date of birth, blood type, race, etc
Store physician names and contact information
Store allergies
Store a list of vaccinations
Store vital signs such as temperature, blood pressure, pulse, respiratory rate, "pain" level, glucose level, cholesterol, height, weight, etc
Store insurance information including list of approved doctors approved labs, approved drugs, approved generic drugs, health care coverage, out of pocket costs, co-pay costs
Payment methods- credit, debit, prepaid, checking account number
Store prescriptions
Store doctors' orders for use of prescriptions
Pay for prescriptions
Store XRays
Store lab results
Pay for lab tests
Store hospital ID bracelet
Store medication used in hospital
Schedule of doctor appointments
Store organ status and donor information
Transfer digital medical artifacts (e.g medical ID, basic patient information, patient contact information, emergency contact information, primary care physician information, health insurance information including co-pay and deductibles, prescriptions, office visit summary, appointment cards, Electronic Medical Records (EMR), lab results, blood type, organ/donor status, vital signs, diagnostic data, immunization records, payments and transaction history, pictures, etc) to remote devices Some of the challenges that an NFC enabled mobile device can address include, but are not limited to the following use cases:

Elderly/Senior Citizens—They may have a sudden health care need with a sensitive need to have a list of medical information, allergies, and prescriptions readily available for urgent health care. Care givers may not have access to their medical information.

ER Patients Their identity may not be known when they arrive at ER and require emergency medical treatment. So, it is urgent to identify who they are, medical history, allergies, and prescriptions, etc.

New Patients—If a new patient is visiting a new doctor for a diagnosis and potentially time sensitive, treatment, patients will need to have medical information, allergies, and prescriptions readily available which may take weeks to receive from previous physician.

Children—Children may not have an ID with them and be on a field trip, sporting event, camping trip, friend's house, etc. So, if there is a health issue, it will be important to be able to confirm their identity, medical information, allergies, and prescriptions readily available for urgent health care, etc.

Frequent international travelers- Frequent travelers need to track their shots and immunizations for travel abroad. If they may have a sudden health care need, they will need to have access to medical information, allergies, and prescriptions readily available for urgent health care.

Patients with Alzheimer's or other conditions that impact memory. They may get lost and not remember who they are or how to get back home or have any identification with them. So, they health care professionals will need to be able to identify them as well as their medical history, allergies, and prescriptions readily available for urgent health care.

Critically serious patients in ICU or prenatal may have require very specific medications and dosages.

Patients who require daily or constant monitoring for insulin levels, asthma, high blood pressure, heart pace maker, etc.

This invention enables patients and health care professionals (nurse, doctor, pharmacist, etc) to manage digital medical artifacts medical digital artifacts (e.g. medical ID, basic patient information, patient contact information, emergency contact information, primary care physician information, health insurance information including co-pay and deductibles, prescriptions, office visit summary, appointment cards, Electronic Medical Records (EMR), lab results, blood type, organ/donor status, vital signs, diagnostic data, immunization records, payments and transaction history, pictures, etc) using an NFC enabled mobile device. : This is accomplished when the user holds, "waves", or "taps" their NFC enabled device in proximity to an NFC Point-Of-Presence (POP) device, Point-Of-Entry (POE), Point-Of-Sale (POS) device, smart poster, or another NFC enabled device. Upon doing so, the POP/POE/POS/etc activates the secure element associated with the NFC enabled mobile device and powers the secure element through induction. So, the secure element need not have its own power source nor does the secure element require use of the battery inside of the mobile device. Correspondingly, if the battery in the mobile device is dead, the user may not be able to use the mobile device to place a phone call, receive an SMS, or surf the web, but they will be able to transfer information from their secure element (e.g. medical ID) since the secure element is powered by the remote NFC enabled POP/POS/POE device. The secure element can also receive digital artifacts from a POP/POS/POE device such as Xrays, prescriptions, appointment cards, etc even if the battery inside of the mobile communication device lacks power. This communication is specified, for example, in the ISO 14443A/B standard and ISO 15693 just to name a few.

BRIEF DESCRIPTION OF THE DRAWINGS

FIGS. 2B1, 2B2A, 2B2B illustrate more details regarding certain components illustrated in FIG. 1.

FIG. 7 illustrates secure element applications

DETAILED DESCRIPTION OF PREFERRED EMBODIMENTS

Reference will now be made in detail to various embodiments, examples of which are illustrated in the accompanying drawings. In the following detailed description, numerous specific details are set forth in order to provide a thorough understanding of the present inventions. However, it will be apparent to one of ordinary skill in the art that the present inventions may be practiced without these specific details. In other instances, well-known methods, procedures, components, and circuits have not been described in detail so as not to unnecessarily obscure aspects of the embodiments.

An NFC enabled device is one that includes a secure element and enables contactless transactions which have been described in more detail in previous patents including U.S. patent application Ser. No. 13/184,246 , entitled "Using a mobile device to enable purchase of deals and increase customer loyalty" filed on Jul. 15, 2011, U.S. Provisional Patent Application No. 61/445,667, entitled "Non-Wireless Bidirectional Communication Between a Mobile Device and Associated Secure Element using an Audio Port" filed on Feb. 23 2011 and U.S. Provisional Patent Application No. 61/429,246, entitled "Wireless Bidirectional Communications between a Mobile Device and Associated Secure Element using Inaudible Sound Waves," filed Jan. 3, 2011 both of which are a continuation in part of U.S. patent application Ser. No. 12/948,717, entitled "Wireless Bidirectional Communications between a Mobile Device and Associated Secure Element," filed Nov. 17, 2010, U.S. patent application Ser. No. 12/592,581 entitled "Method and Apparatus For Completing A Transaction Using A Wireless Mobile Communication Channel and Another Communication Channel", filed Nov. 25, 2009, U.S. patent application Ser. No. 11/948,903, entitled "Method And System For Conducting An Online Payment Transaction Using A Mobile Communication Device " filed on Nov. 30, 2007, U.S. patent application Ser. No. 11/939,821, entitled "Method and System for Securing Transactions Made Through a Mobile Communication Device" filed Nov. 14, 2007, and U.S. patent application Ser. No. 11/933,351 entitled "Method and System for Purchasing Event Tickets Using a Mobile Communication Device", filed Oct. 31, 2007, and U.S. patent application Ser. No. 11/933,321 entitled "Method and System for Adapting a Wireless Mobile Communication Device for Wireless Transactions," filed Oct. 31, 2007 all of which are a continuation-in-part of U.S. patent application Ser. No. 11/467,441, entitled "Method and Apparatus for Completing a Transaction Using a Wireless Mobile Communication Channel and Another Communication Channel," filed Aug. 25, 2006, which claims priority to U.S. Provisional Patent Application Nos. 60/766,171 and 60/766,172, both of which were filed Dec. 31, 2005. All of the above-referenced patent applications are incorporated by reference herein in their entirety.

Figure 1:
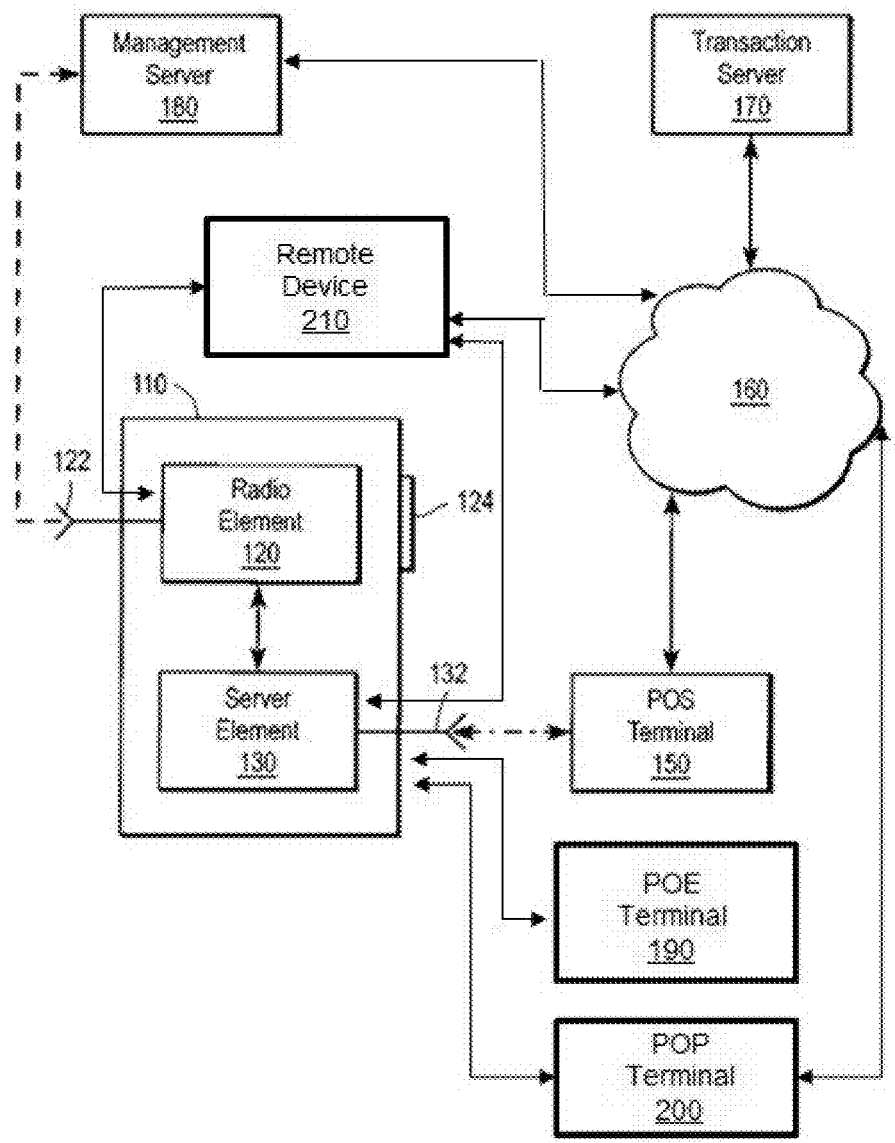
FIG. 1 illustrates a block diagram of a communication system including a wireless mobile communication device and a management server in accordance with one implementation.
Figure 2:
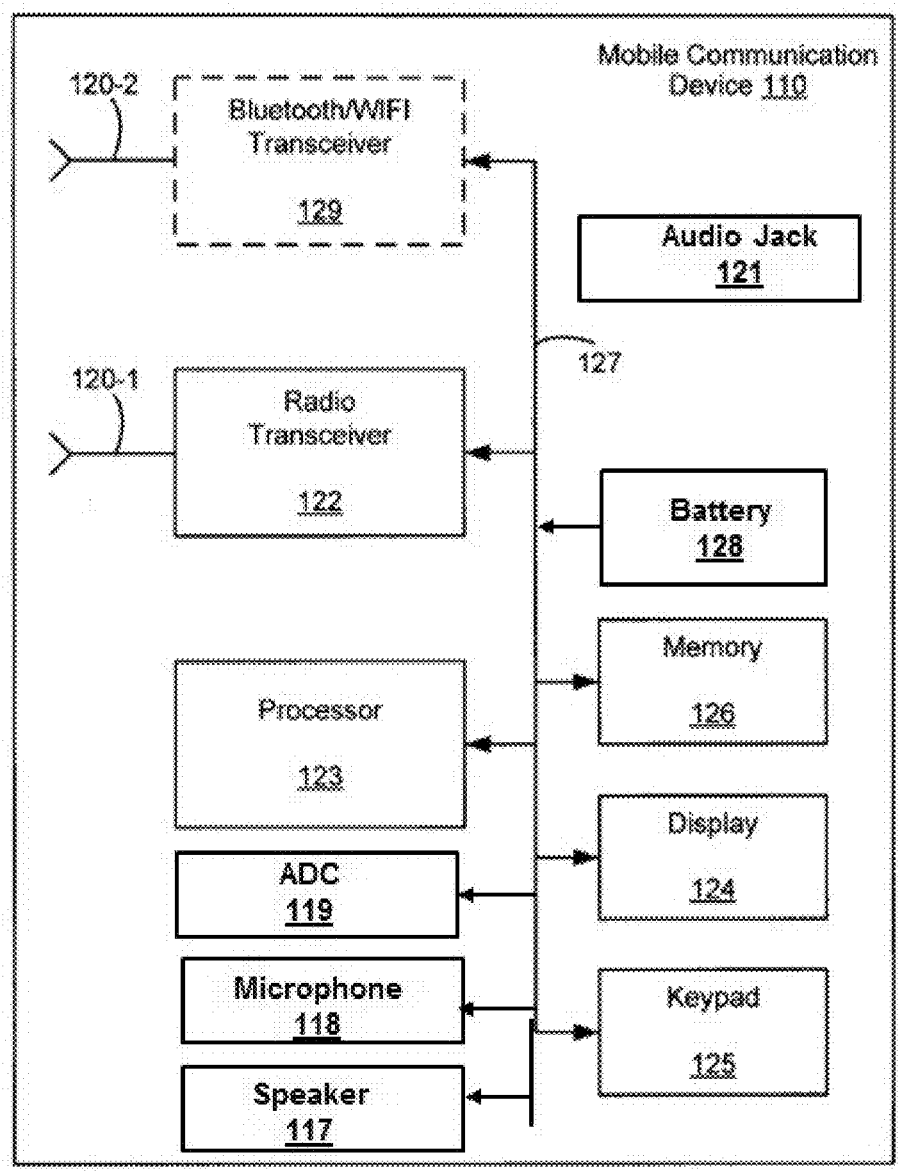
FIG. 2 illustrates a block diagram of a mobile communication device in accordance with one implementation.

As previously described in U.S. patent application Ser. No. 12/592,581, entitled "Method and Apparatus For Completing A Transaction Using A Wireless Mobile Communication Channel and Another Communication Channel", filed Nov. 25, 2009 which is a continuation in part of U.S. patent application Ser. No. 11/467,441, entitled "Method and Apparatus For Completing A Transaction Using A Wireless Mobile Communication Channel and Another Communication Channel", filed Aug. 25, 2006, FIG. 1 is a block diagram illustrating a communication system 100 in accordance with some embodiments. The communication system 100 includes a hand-held, wireless mobile communication device 110 with an antenna 120 for wireless communication. While the antenna 120 is shown as extending from the mobile communication device 110 for visual clarity, the antenna 120 may be implemented internally within the mobile communication device 110. Also, the mobile communication device 110 may include more than one antenna 120. The mobile communication device 110 includes a user interface for entering data. For example, a display 124 (FIG. 2) is a touch-screen display; alternatively or in addition, the mobile communication device 110 includes a keypad 125 (FIG. 2) for entering data.

A preferred embodiment, both the radio element 120 and the secure element 130 are both disposed internally within a body of the mobile device 110 as illustrated in FIG. 1, although in certain embodiments the secure element 130 can be external to the mobile device 110 as described hereinafter. In a variant implementation, the mobile device 110 contain a slot, which allows for the insertion of a secure element 130 into a slot and thus the physical insertion, mechanical and electrical connection as needed. In this configuration, the secure element can be purchased independently of the mobile device 110. The secure element 130 can also be disposed into a slot that only provides for physical insertion and mechanical connection to the body of the mobile device 110, and can then preferably include a transceiver that allows for the communication with the radio element 130 using a wireless local communication channel.

The radio element 120 also is illustrated as optionally including another transceiver 129, such as a Bluetooth or WIFI transceiver, which can transmit and receive signals with an external device and then communicate signals to and from the radio processor 123. This additional communication channel allows for communications between other external devices, such as an external Bluetooth enabled smartcard, and provides an additional communication channel that is useful for certain transactions, as described further herein.

FIG. 2B1 illustrates a preferred embodiment of the secure element 130 associated with the mobile device 110, the secure element 130 being commonly known as a smart card. As illustrated, the secure element 130 has a secure processor 132, a secure memory 133 and a POS/NFC transceiver 134 adapted to send transaction request signals and receive transaction response signals over a first communication channel. The secure processor 132 communicates via the secure element driver 128 with the radio processor 123, using, as mentioned above, signals described in the Java Card 2.1 Platform API Specification. The transaction request signals and the transaction response signals associated with the transaction preferably include identification code associated with the user, as well as information relative to the transaction, such as item, quantity, vendor, as is known. The POS transceiver 134 is preferably an NFC device of some type, which uses an NFC modem, although it can also be a Bluetooth, WIFI or other transceiver. In the case of the implementation of the POS transceiver being an NFC modem, such an NFC modem will typically have a set of registers that can be read/written by the secure processor 132. These registers are in turn available for reading and writing over the RFID communications channel and serve as a sort of shared memory between the secure processor 123 within the secure element 130 and the RFID reader that is associated with the POS terminal 150. This communication is specified, for example, in the ISO 14443A/B standard and ISO 15693 just to name a few.

Illustrated in an alternative embodiment is the inclusion of a radio/Bluetooth/WIFI transceiver 136, which can communicate with other devices, such as a transceiver associated with the radio processor 120 or for other external devices having those communication capabilities, thus allowing for more flexibility.

FIG. 2B2A shows a modified secure element 130, in which the radio element 120 does not communicate with the secure element through a secure element driver 128 of some type. In this case, for example, the secure element 130 may be external to the mobile device 110 and as such is not connected to the radio element through the secure element driver 128. In such an implementation, however, if the transceiver 136 as described above is included, and a similar transceiver 129 associated with the radio element 130 as described previously with respect to FIG. 1 is included, then this communication channel can be used to wirelessly obtain direct communications between the radio element 120 and the secure element 130.

This implementation allows for certain bidirectional communications with other devices, as well as with the radio element 120, and as such more functionality and flexibility is achieved. This implementation is particularly useful since it establishes a direct local communication path with the radio element 120, since there is not communications with the radio element 120 via the path of driver 128.

If either of the transceivers 129 or 136 are not associated with the respective radio element 120 or secure element 130, and there is no direct connection between the radio element 120 an the secure element 130, then a direct communication link between the radio element 120 an the secure element 130 will not exist. As such, while ticketing and many transactions can still exist, data from a real-time transaction performed using the secure element 130 cannot be made directly available to the radio processor and the applications stored thereon, which can prevent, for example, certain redundancy checks to occur, such as a ticketing application in which, after the ticket order has been placed, the ticketing application in the memory 126 associated with the radio element 130 can be programmed to provide an alert if the ticket receipt, via the management server 180, has not been received within a certain period of time. Such an alert would not be possible to program directly (although it could be programmed indirectly via the button panel on the phone, though such an implementation requires extra user intervention, which, if possible, one attempts to avoid in transactions such as this.

FIG. 2B2B shows a modified secure element 130", in which the secure element does not include a processor that is capable of bidirectional communications, but instead is a passive device 138', such as an RFID sticker or some other tag, that allows for a user identification, such that a transaction that is initiated with the passive device 138' will cause the management server 180 to perform the transaction details. In this implementation, the code received from the POS terminal 150 or the POE terminal 190 is transmitted from the POS terminal 150 or the POE terminal 190 to the management server 180, which then takes over the transaction. This passive device 138', with the identification code stored thereon, can thus be associated with a mobile device 110 not otherwise equipped for such communications, and the management server 190 can provide transactional information to the mobile device 110 using available channels on the mobile device (such as audio, sms or other known data transmission methods). While bidirectional communications do not occur with other devices, transactions are possible, because the management server 190 is involved.

Figure 3:
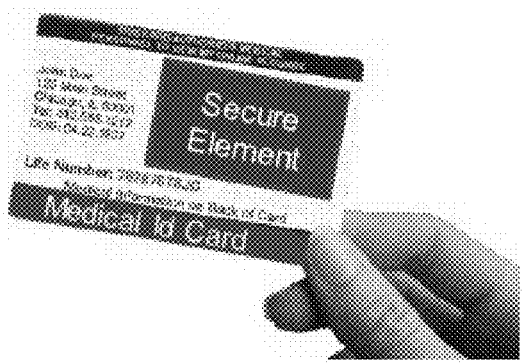
FIG. 3 illustrates a secure element embedded in an ID card
Figure 4:
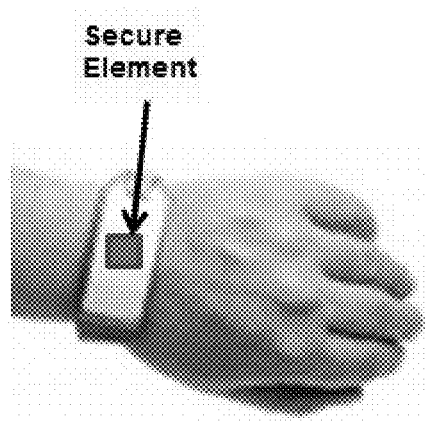
FIG. 4 illustrates a secure element embedded in a wristband

FIG. 2B2C illustrates a secure element that is capable of either two-way communication or one-way communication with a POS/POE device that is not affixed to a mobile device nor electrically coupled to the mobile device. Instead the secure element is affixed to a hospital bracelet. FIG. 3 illustrates a secure element that is affixed to a affixed to a plastic medical ID card and FIG. 4 illustrates a secure element affixed to a affixed to a hospital bracelet, for example. Similarly, a secure element that is not affixed to a mobile device nor is electrically coupled to a mobile device can be incorporated with a key chain, watch, ring, bracelet worn as jewelry.

Figure 5:
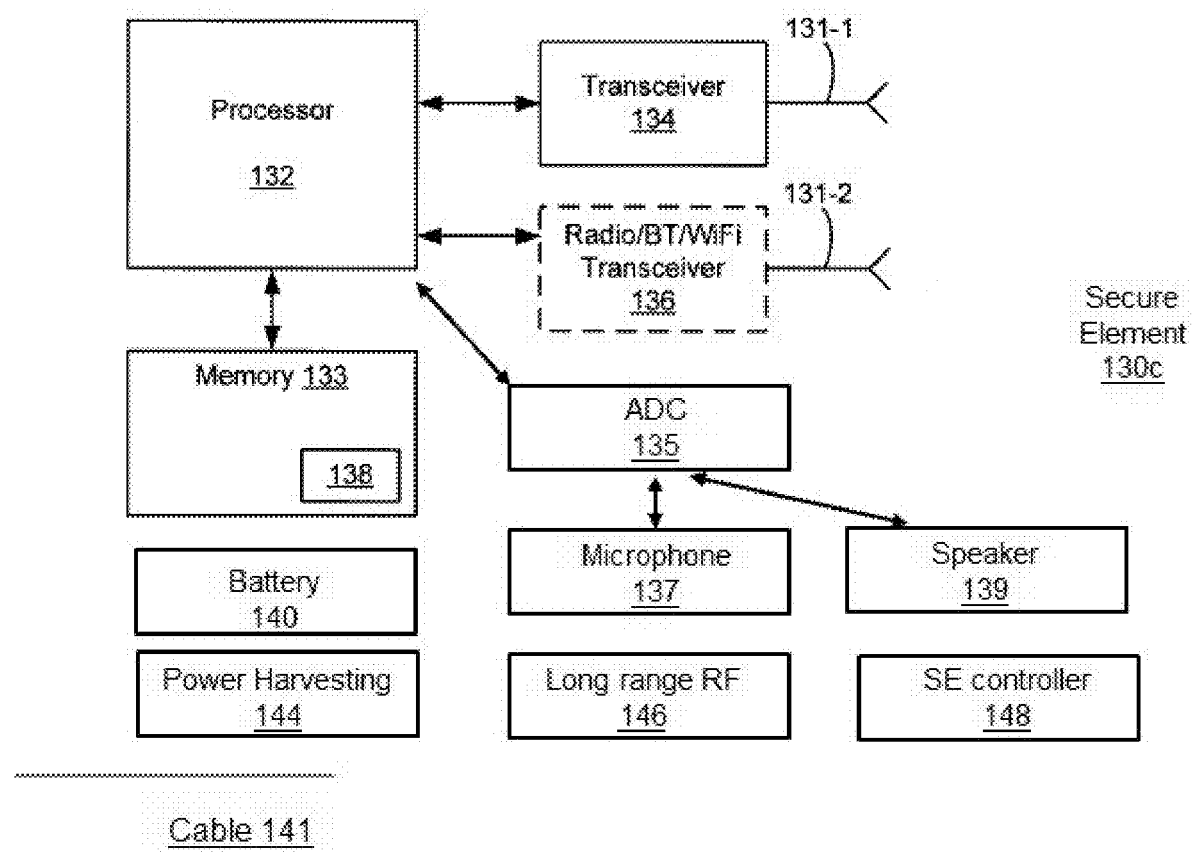
FIG. 5 illustrates more details regarding certain components of a secure illustrated in FIG. 1 of a secure element that is capable of bi-directional communication with a mobile device and transfer of data to a remote server
Figure 6:
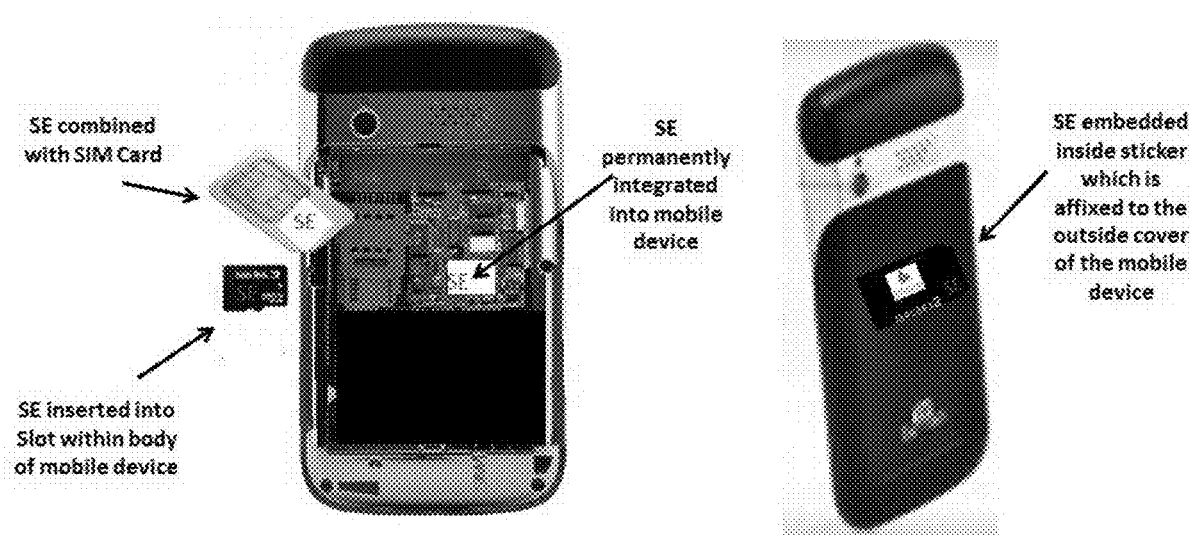
FIG. 6 illustrates multiple secure elements coupled to a mobile communication device

As illustrated in FIG. 5, and enhanced secure element 130 that is capable of bi-directional communication with a mobile device has a secure NFC processor 132, a secure memory 133 and a POS/NFC transceiver 134 adapted to send transaction request signals and receive transaction response signals over a first communication channel. A/D converter 135, a microphone 137, a speaker 139, and a, cable 141, power harvester, 144, Long range RF transceiver, 146, and a SE controller, 148. The Secure Element Controller 148 can either be logical or physical. In a logical implementation, it simply utilizes the primary secure element transceiver 134, memory 133 with data and applications, and a processor 132 to communicate with multiple logical or physical secure elements. Stated another way, the Secure Element Controller is the parent controller and all of the other logical or physical secure elements. The Secure Element Controller can issue read/write commands to all of the other logical or physical secure elements.

As described above, the secure element 130 has a secure processor 132, a secure memory 133 and a POS or NFC transceiver 134 adapted to send transaction request signals and receive transaction response signals over a first communication channel. In some embodiments a secure element 130 is internal to the mobile communication device 110. In some embodiments, the secure element 130 is externally attached to the mobile communication device 110. For example, the secure element 130 is adhesively affixed or mechanically secured to the housing of the mobile communication device 110. Alternatively, the secure element 130 is housed within a slot in the mobile communication device 110. The secure element 130 includes an antenna 131 for wireless communication. While the antenna 131 is shown as extending from the secure element 130 for visual clarity, the antenna 131 may be implemented internally within the secure element 130. Also, the secure element 130 may include more than one antenna 131. Communication occurs wirelessly between the secure element 130 and the mobile communication device 110 via respective antennas 120 and 131, over a direct wireless channel 163 between the mobile communication device 110 and the secure element 130. Thus, in some embodiments, the channel 163 does not pass through a network.

The point of sale terminal 150 illustrated in FIG. 1 is conventional, in that it has the capability of electronically reading information from a device equipped to transmit information in a format that it reads. Thus, the reader (not shown) within the point of sale terminal 150 can be of one or many types. If the point of sale terminal reader (not shown) includes the provision for NFC communications, then simply bringing the secure element 130 with the NFC transceiver will cause initiation of a transaction and the transmission of the identification code associated with the secure element 130 and thus the user.

For the embodiments described above, various software that is downloaded into the memory 126 of the radio element 120 and the secure memory 132 of the secure element 130, along with software resident on the management server 180, will cooperate at a layer that is above the physical layer of the communications, in order for the desired transaction to occur. This software is implemented using based upon known knowledge of mobile device 110 internals and application platforms, NFC, smartcard internals and application platforms, payment protocols (e.g. PayPass), and the working/workflow associated with POS and POE terminals, and the transaction and management servers. In addition, the present invention provides for piggybacking a tunneling protocol on top of the payment protocol, so that the secure elements 130 can communicate with the transaction server 170 and/or the management server 180, without modification to the POS terminal 150 or the POE terminal 190. As such, this includes software within the secure element 130 that embeds the required information in fields which will not adversely affect the performance of the POS terminal 150 and/or the POE terminal 190, and also software in transaction server 170 that will extract the piggybacked payload, associate the payload with the management server 180 if needed, and then authenticate, authorize, and execute transfers of transaction information to the management server 180.

In another embodiment, the piggybacked payload is sent, instead of to the transaction server 170, to the management server 180, which can then associate the transaction and notify the transaction server 170, the POS terminal 150 and/or the POE terminal as needed.

There are several types of NFC transactions. First, when the secure element is held in proximity to a remote device (i.e. Point-Of-Sale (POS) device 150, Point-Of-Entry (POE) 190, Point-Of-Presence (POP) device 200, smart poster, another secure element, etc) the POS/POE/POP activates or powers the secure element 130 through induction and triggers an application residing in the secure element (which is different than an application residing on the mobile communication device . So, the secure element need not have its own power source nor does the secure element require use of the battery inside of the mobile device. Stated another way, if the battery in the mobile device is dead, the user may not be able to use the mobile device to place a phone call, receive an SMS, or surf the web, but they will be able to purchase item and receive coupons and other digital artifacts using the secure element since the secure element is powered by the remote NFC enabled POS/POE/POP device. To reiterate, after triggering the secure element, an application residing in the secure element (which is different than an application residing on the mobile communication device) is launched and the application can transfer digital artifacts to the POS/POE/POP and the POS/POE/POP terminal can transmit digital artifacts to the secure element again even if the battery inside of the mobile communication device lacks power. There are instances when the NFC enabled mobile device is active and it can power any NFC device in passive mode including a POS/POE/POP, smart poster, or another NFC enabled mobile device which will described in more detail further herein.

While a POS may receive payment credentials from the secure element which is processed by the transaction server 170, the POS may transfer a coupon, receipt, or some other digital artifact to the secure element simultaneously during the induction process from the POS terminal 150, the transaction server 170 or the management server 180. Stated another way, the user need only hold , "wave" or "tap" their NFC enabled device once near the POS and both the transmission of the ticket to the POP and the receipt of the digital artifact will occur simultaneously so the user will not have to "tap" or "wave" their phone twice. This is accomplished through induction as well. The POS device/terminal will activate the secure element and an application residing in the secure element (which is different than an application residing on the mobile communication device) will facilitate the transfer.

As mentioned previously a Point-Of-Entry (POE) terminal is also equipped with NFC. When a user holds, "waves", or "taps" their NFC enabled device near a POE terminal, the POE terminal activates the secure element in the NFC enabled mobile device and triggers an application in the secure element to transfer a ticket, for example, to the POE device which enables the user to gain access to the venue, building, automobile, etc.

While an NFC enabled Point of Sale (POS) facilitates a contactless purchase or financial transaction and a Point-of-Entry (POE) terminal facilities contactless access, an NFC enabled Point of Presence (POP) facilitates contactless transaction. A POP device is similar to an NFC POS enabled device in that it does contain a secure element and is capable of NFC communications (including two way communications). A POP is also capable of induction to be able to power an NFC enabled mobile communication device held in proximity to it and triggers an application running in the secure element to transfer information from the NFC enabled mobile communication device to the POP. Some examples of POPs include a kiosk, automobile, hotel, house, smart poster, smart catalogue, computer, medical device, another NFC mobile device, a music player, products at a retail store, etc. One example is a user holds their NFC enabled device near a kiosk which powers the secure element and launches an application to transmit a free song from the kiosk to the secure element. The POP can send/receive transaction data to the management server, 180, have transactions processed by the transaction server 170, or transfer/receive digital artifacts to/from the secure element 130 at the remote server 210.

A POP may be a Smart Poster- When an NFC enabled mobile communication device is held in proximity to a smart poster, the smart poster may transmit information, data, maps, or any other type of digital artifact to the secure element.

A POP may be a computer, laptop, tablet, etc-. A user first uses the mobile wallet to select which items to be transferred to the POP and instructs the user to hold the NFC device near the POP. When an NFC enabled mobile communication device is held in proximity to the computer, the computer can transmit information, data, maps, or any other type of digital artifact to the secure element A POP may be another NFC Enabled Mobile communication device. A user first uses the mobile wallet to select which items to be transferred to the POP and instructs the user to hold the NFC device near the POP. When an NFC enabled mobile communication device is held in proximity to another NFC enabled device may transmit contact information, email, web site addresses, social media information, tickets, coupons, receipts, vouchers, content, or any other type of digital artifact to the secure element As described in U.S. patent application Ser. No. 13/213,840 entitled "Transferring Data Between NFC Enabled Mobile Devices With Multiple Secure Elements" filed on Aug. 19, 2011 which is incorporated herein by reference, after a user holds an NFC enabled mobile device in proximity to an NFC POS/POE/POP, the NFC POS/POE/POP can transfer secondary digital artifacts to the secure element such as Xrays, tickets, business cards, music, product information, etc. As described in more detail in the patent applications mentioned above, a user may have to authenticate and the secure element may have to be unlocked prior to the storage of digital artifacts in the secure element. For security purposes, the secure element keys are located at the management server, 180 and may be managed by an entity sometimes referred to as a "Trusted Server Manager". In cases where network availability is not reliable and performance is critical, the secure element key may be downloaded to the mobile device in an encrypted file. This communication is specified, for example, in the ISO 14443A/B standard and ISO 15693 just to name a few As mentioned previously, an NFC enabled mobile communication device may have multiple secure elements. There may be a secure element may be dedicated to specific financial transactions vs another secure element which may be dedicated to medical records and have a separate secure element key. There may even be a secure element that is "public domain" which any POS or device can write to without any restricted accesses. As shown in FIG. 7, there can be a different "health care secure element software application; for different functions. There may be 1 logical secure element or multiple secure elements as described in U.S. patent application Ser. No. 13/213,840, entitled "Transferring Data Between NFC Enabled Mobile Devices With Multiple Secure Elements" filed on Aug. 19, 2011. There may be a secure element and application for prescriptions, office visits, appointments, EMR, pictures, etc. A user may only need to tap once to transfer artifacts to multiple secure elements. Alternatively, a user may tap once to transfer an ID, for example, from the secure element to the POP and then tap another time to transfer artifacts from the POP such as a prescription from the POP to the secure element. The transfer of digital artifacts between secure element and a POP is a result each application stored in the secure element having its own Id. So for example, a secure element application that facilitates transfer of a patient's medical ID to/from a secure element may have an ID of "SE_App1. In contrast, a secure element application that facilitates transfer of prescriptions to/from a secure element may have an ID of "SE_App3". Whenever multiple applications exist in the secure element, the applications must be prioritized so that the POP/POS/POE will know which application to trigger and in which order. So, for example if the user selects to get a prescription using their mobile wallet, the mobile wallet will transfer a signal to the secure element to make the "X ray secure element application or SE_App3" the active one and assign it priority of 1 so that the POP/POS/POE will select it first. The mobile wallet communicates to the secure element in a number of different ways regardless of whether secure element is internal ,inserted into a slot within the body of the mobile device, or affixed externally to the body of a mobile device as described in U.S. Provisional Patent Application No. 61/445,667, entitled "Non-Wireless Bidirectional Communication Between a Mobile Device and Associated Secure Element using an Audio Port" filed on Feb. 23, 2011 and U.S. Provisional Patent Application No. 61/429,246, entitled "Wireless Bidirectional Communications between a Mobile Device and Associated Secure Element using Inaudible Sound Waves," filed Jan. 3, 2011 both of which are a continuation in part of U.S. patent application Ser. No. 12/948,717, entitled "Wireless Bidirectional Communications between a Mobile Device and Associated Secure Element," filed Nov. 17, 2010 which are incorporated by reference herein In one embodiment, a POP 200 (i.e. medical device) can include secure element that is pre-installed or embedded in the medical device for a wired connection (e.g. USB or serial) or a wireless connection (e.g. NFC, Bluetooth, WIFI, infrared, inaudible sound waves using a speaker and microphone, etc). In this way, the data from the medical can be transmitted to the mobile device 110 coupled to (e.g. the patients mobile device), another mobile device 210 (e.g. the physicians mobile device), server 170, POS 150, POE 190, another POP 200 (e.g. medical , EMR) using USB, Serial Port, NFC, WIFI, Bluetooth, Infrared, inaudible sound as described in U.S. patent application Non-Wireless Bidirectional Communication Between a Mobile Device and Associated Secure Element using an Audio Port" filed on Feb. 23, 2011, U.S. patent application Ser. No. 13/223,233, " Using an NFC Enabled Mobile Device To Manage Health Care" filed on Aug. 31, 2011" and U.S. patent application Ser. No. 13/218,879 entitled "Using an NFC Enabled Mobile Device To Manage Digital Medical Artifacts" filed on Aug. 26, 2011.

In another embodiment, the POP 200 (i.e. medical device) may be connected to an externally coupled secure element through a "universal health port" 144 is installed on the medical device using a wired connection such as USB, serial port, or audio port as described in U.S. patent application Non-Wireless Bidirectional Communication Between a Mobile Device and Associated Secure Element using an Audio Port" filed on Feb. 23, 2011.

Alternatively, the POP 200 (i.e. medical device) may be connected to an externally coupled secure element through theuniversal health port using a wireless connection (e.g. NFC, Bluetooth, WIFI, infrared, inaudible sound waves using a speaker and microphone, etc) . as described in U.S. Provisional Patent Application No. 61/429,246, entitled "Wireless Bidirectional Communications between a Mobile Device and Associated Secure Element using Inaudible Sound Waves," filed Jan. 3, 2011 both of which are a continuation in part of U.S. patent application Ser. No. 12/948,717, entitled "Wireless Bidirectional Communications between a Mobile Device and Associated Secure Element," filed Nov. 17, 2010, or some other conventional port. The secure element can include WIFI, NFC, Bluetooth, infrared, inaudible sound waves using a speaker and microphone as described in U.S. patent application number, or a combination of these.

In either case regardless of whether the POP, 200 (i.e. medical device) has an embedded secure element or a coupled secure element connected to the universal health port using a wired connection or a wireless connection, data/digital artifacts can be transferred from the medical device to the secure element using any number of conventional protocols such as USB, Serial Port, NFC, WIFI, Bluetooth, Infrared, inaudible sound waves, etc. Once the data/digital artifacts are at the secure element, they can be transferred from the secure element to the mobile device 110 coupled to (e.g. the patients mobile device), another mobile device 210 (e.g. the physicians mobile device), server 170, POS 150, POE 190, another POP 200 (e.g. medical, EMR) using USB, Serial Port, NFC, WIFI, Bluetooth, Infrared, inaudible sound as described in U.S. patent application Non-Wireless Bidirectional Communication Between a Mobile Device and Associated Secure Element using an Audio Port" filed on Feb. 23, 2011, U.S. patent application Ser. No. 13/223,233, "Using an NFC Enabled Mobile Device To Manage Health Care" filed on Aug. 31, 2011" and U.S. patent application Ser. No. 13/218,879 entitled "Using an NFC Enabled Mobile Device To Manage Digital Medical Artifacts" filed on Aug. 26, 2011.

Figure 8:
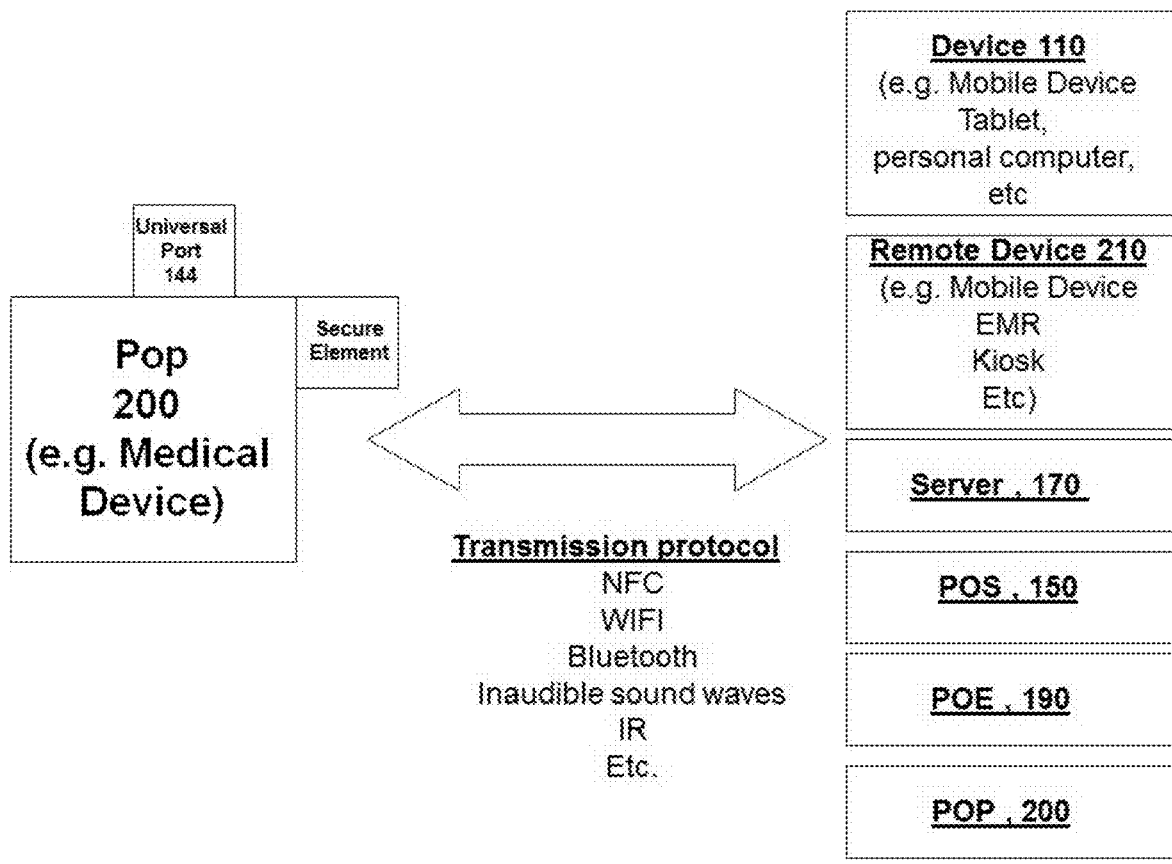
FIG. 8 illustrates medical devices with an externally affixed secure element

After the mobile device receives the data/digital artifacts, it can be displayed in the mobile device 110 or the remote mobile device 210 and/or transmitted to another mobile device (e.g. the patients mobile device, the health care provider's mobile device, server,), server, Electronic Medical Records, tablet, another medical device, etc as depicted in FIG. 8.

In one embodiment, when a Health Care Provider wants to extract data from a medical device using NFC, the health care providers NFC enabled mobile device (i.e. mobile device with embedded NFC, NFC in a slot, NFC smart sicker) powers or activates the secure element application located inside the secure element of the medical device which has either an embedded NFC or externally coupled secure element. In doing so, the medical device secure element application transfers data to the health care providers NFC enabled mobile device as described in U.S. patent application Ser. No. 13/223,233, "Using an NFC Enabled Mobile Device To Manage Health Care" filed on Aug. 31, 2011" and U.S. patent application Ser. No. 13/218,879 entitled "Using an NFC Enabled Mobile Device To Manage Digital Medical Artifacts" filed on Aug. 26, 2011.

In another embodiment, the Health Care Provider's mobile device simply has a secure element with only an NFC transceiver. When a Health Care Provider wants to extract data from a medical device with the secure element coupled to it, the health care provider "waves" or "holds" their mobile device which only has an NFC transceiver near the medical device with the coupled secure element. In doing so, the secure element coupled to the medical device activates an application running on the health care provider mobile device (not the secure element) which subsequently connects to an application on a remote server for processing. Alternatively, the NFC transceiver may simply execute an application stored on a remote server bypassing an application on the mobile device. In this way, the health care provider's mobile device need not have a full secure element with its own memory and a secure element application. Stated another way, the NFC transceiver in the Health Care Provider's mobile device is simply used as a trigger to execute an application either stored on the mobile device and/or stored on a server when it is brought into proximity of a medical device which has a secure element to trigger the NFC transceiver via NFC induction. This approach enables the health care provider to utilize applications stored on the management server which is more scalable since the applications that reside on a server can be easily added, changed, etc.

For example, if the Health Care Provider (HCP) wishers to update a patients EMR records stored at he server with the data from the medical device, the Health Care Provider waves their mobile device near the medical device with the coupled secure element and upon doing so, the EMR application on the Health Care Provider mobile device launches and connects to the EMR application on the server to automatically transfer the measurement/sensor data from the medical device to the HCP mobile device and to the server using conventional wireless service.

In cases where security is required to capture and transfer the data, the techniques described as described in U.S. patent application Ser. No. 13/223,233, entitled " Using an NFC Enabled Mobile Device To Manage Health Care" filed on Aug. 31, 2011" and U.S. patent application Ser. No. 13/218, 879 entitled "Using an NFC Enabled Mobile Device To Manage Digital Medical Artifacts" filed on Aug. 26, 2011.

In some embodiments, digital artifacts can be removed from the secure element coupled to the medical device as described in U as described in U.S. patent application Ser. No. 13/223,233, entitled, "Using an NFC Enabled Mobile Device To Manage Health Care" filed on Aug. 31, 2011" and U.S. patent application Ser. No. 13/218,879 entitled "Using an NFC Enabled Mobile Device To Manage Digital Medical Artifacts" filed on Aug. 26, 2011.

In some embodiments, the mobile wallet which is running on the mobile device/smart phone displays data transmitted from the medical device can include digital artifacts as described in U.S. patent application Ser. No. 11/956,261 entitled "Method and System for Delivering Customized Information To A Mobile Communication Device Based on User Affiliations", filed Dec. 13, 2007

What is claimed is:

1. A method for transmitting a medical digital artifact to a mobile device, the method comprising:

executing a first secure element application on a processor of a first secure element coupled to a medical device externally coupled to a body in response to a Near Field Communication (NFC) inductive signal by a second secure element coupled to the mobile device, wherein the first secure element is connected to the medical device via a universal port, the first secure element application configured to use a near field communication protocol;

wirelessly transmitting the medical digital artifact from first secure element coupled to the medical device using the first secure element application, through a first communication channel configured to use the NFC protocol to the second secure element coupled to the mobile device; and displaying the medical digital artifact within a the non-browser based mobile application maintained on the mobile device, wherein the non-browser based mobile application is a mobile operating system platform non-browser based mobile application with a graphical user interface that is preinstalled or downloaded and installed on the mobile device, wherein the graphical user interface includes a graphical icon, wherein the mobile device comprises a mobile device transceiver, a mobile device display, and a mobile device memory which maintains the non-browser based mobile application.

2. The method of claim 1, wherein the medical digital artifact comprises one or more of information related to a medical id, information related to patient information, information related to a prescription, information related to emergency contact information, information related to physician information, information related to a vital sign, information related to insurance information, information related to an office visit summary, information related to an appointment, information related to an Electronic Medical Records (EMR), information related to a lab result, information related to blood type, information related to organ/donor status, information related to diagnostic data, or information related to an immunization record.

3. The method of claim 2, wherein patient information includes one or more of information related to gender, information related to age, information related to date of birth, information related to blood type, information related to race, information related to contact lenses, information related to an implant, or information related to a pacemaker.

4. The method of claim 2, wherein the vital sign includes one or more of information related to temperature, information related to blood pressure, information related to pulse, information related to respiratory rate, information related to pain level, information related to glucose level, information related to cholesterol, information related to height, or information related to weight.

5. The method of claim 2, wherein the insurance information includes one or more of information related to a doctor, information related to a lab, information related to a drug, information related to a generic drug, information related to health care coverage, information related to out of pocket costs, or information related to co-pay costs.

6. The method of claim 1, wherein the first secure element is coupled to the universal port using a Universal Serial Bus (USB).

7. The method of claim L wherein the first secure element is coupled to the universal port using a wireless connection.

8. The method of claim 7, wherein the wireless connection comprises one of NFC, Bluetooth, or WIFI.

9. The method of claim 1, further wherein the medical digital artifacts is stored in a first secure element memory different than a second secure element memory that the secure application is stored in.

10. The method of claim 1, wherein different secure element applications are stored in different secure elements, and further wherein a secure element controller manages the different secure element applications.

11. The method of claim 1, further wherein upon the condition that the mobile device loses connection with a wireless network, the non-browser based mobile application monitors for access to the wireless network and automatically reconnects to the wireless network when the wireless network is available.

12. The method of claim 1, further wherein the non-browser based mobile application sends an alert if it has not received the medical digital artifact within a certain period of time.

13. A system for transmitting a medical digital artifact to a mobile device, the system comprising:
  a secure element processor executing a first secure element application, in response to a Near Field Communication (NFC) inductive signal by the second secure element coupled to a mobile device wherein a the first secure element is coupled to a medical device using a universal port, the first secure element application configured to use a near field communication protocol, the medical device is externally coupled to a body;
  a secure element transceiver for wirelessly transmitting the medical digital artifact associated with the first secure element application, through a first communication channel configured to use the NFC protocol to the second secure element coupled to the mobile device; and
  a mobile device processor for displaying the medical digital artifact within a non-browser based mobile application, wherein the non-browser based mobile application is a mobile operating system platform non-browser based mobile application with a graphical user interface that is preinstalled or downloaded and installed on the mobile device wherein the graphical user interface includes a graphical icon, wherein the mobile device comprises a mobile device transceiver, a mobile device display, and a mobile device memory which maintains the non-browser based mobile application.

14. The system of claim 13, wherein the medical digital artifact comprises one or more of information related to a medical id, information related to patient information, information related to a prescription, information related to emergency contact information, information related to physician information, information related to a vital sign, information related to insurance information, information related to an office visit summary, information related to an appointment, information related to an Electronic Medical Records (EMR), information related to a lab result, information related to blood type, information related to organ/donor status, information related to diagnostic data, or information related to an immunization record.

15. The system of claim 14 wherein patient information includes one or more of information related to gender, information related to age, information related to date of birth, information related to blood type, information related to race, information related to contact lenses, information related to an implant, or information related to a pacemaker.

16. The system of claim 14, wherein the vital sign includes one or more of information related to temperature, information related to blood pressure, information related to pulse, information related to respiratory rate, information related to pain level, information related to glucose level, information related to cholesterol, information related to height, or information related to weight.

17. The system of claim 14, wherein the insurance information includes one or more of information related to a doctor, information related to a lab, information related to a drug, information related to a generic drug, information related to health care coverage, information related to out of pocket costs, or information related to co-pay costs.

18. The system of claim 13, wherein the first secure element is coupled to the universal port using a Universal Serial Bus (USB).

19. The system of claim 13, wherein the first secure element is coupled to the universal port using a wireless connection.

20. The system of claim 19, wherein the wireless connection comprises one of NFC, Bluetooth, or WIFI.

21. The system of claim 13, further wherein the medical digital artifacts is stored in a first secure element memory different than a second secure element memory that the secure application is stored in.

22. The system of claim 13, wherein different secure element applications are stored in different secure elements, and further wherein a secure element controller manages the different secure element applications.

23. The system of claim 13, further wherein upon the condition that the mobile device loses connection with a wireless network, the non-browser based mobile application monitors for access to the wireless network and automatically reconnects to the wireless network when the wireless network is available.

24. The system of claim 13, further wherein the non-browser based mobile application sends an alert if it has not received the medical digital artifact within a certain period of time.

* * * * *